United States Patent
Andersen

(10) Patent No.: US 11,304,647 B2
(45) Date of Patent: Apr. 19, 2022

(54) DYNAMIC CONTROL OF SENSITIVITY ASSOCIATED WITH DETECTING R-WAVES

(71) Applicant: Pacesetter, Inc., Santa Clara, CA (US)

(72) Inventor: Dean Andersen, San Jose, CA (US)

(73) Assignee: Pacesetter, Inc., Sylmar, CA (US)

( * ) Notice: Subject to any disclaimer, the term of this patent is extended or adjusted under 35 U.S.C. 154(b) by 175 days.

(21) Appl. No.: 16/171,112

(22) Filed: Oct. 25, 2018

(65) Prior Publication Data

US 2020/0129082 A1   Apr. 30, 2020

(51) Int. Cl.
| | |
|---|---|
| A61B 5/364 | (2021.01) |
| A61B 5/00 | (2006.01) |
| A61B 5/352 | (2021.01) |
| A61N 1/375 | (2006.01) |
| A61N 1/365 | (2006.01) |

(52) U.S. Cl.
CPC .............. *A61B 5/364* (2021.01); *A61B 5/352* (2021.01); *A61B 5/686* (2013.01); *A61B 2560/0223* (2013.01); *A61N 1/365* (2013.01); *A61N 1/3756* (2013.01); *A61N 1/37512* (2017.08)

(58) Field of Classification Search
CPC ..... A61B 5/0468; A61B 5/0456; A61B 5/686; A61B 2560/0223; A61B 5/0428; A61N 1/37512; A61N 1/365; A61N 1/3756; A61N 1/3704; A61N 1/025; H03M 1/12; H03M 1/181
See application file for complete search history.

(56) References Cited

U.S. PATENT DOCUMENTS

| | | | |
|---|---|---|---|
| 4,768,511 | A | 9/1988 | DeCote, Jr. |
| 5,662,688 | A | 9/1997 | Haefner et al. |
| 5,891,048 | A | 4/1999 | Nigam et al. |
| 5,957,857 | A | 9/1999 | Hartley |

(Continued)

FOREIGN PATENT DOCUMENTS

WO    WO2008/058190 A2    5/2008

OTHER PUBLICATIONS

International Search Report & The Written Opinion of the International Searching Authority dated Dec. 18, 2019, International Application No. PCT/US2019/052388.

(Continued)

*Primary Examiner* — Lynsey C Eiseman
*Assistant Examiner* — Amanda L Steinberg
(74) *Attorney, Agent, or Firm* — Vierra Magen Marcus LLP

(57) ABSTRACT

Devices and methods for dynamically controlling sensitivity associated with detecting R-waves while maintaining the fixed detection threshold are described herein. One such method includes sensing an analog signal indicative of cardiac electrical activity, converting the analog signal indicative of cardiac electrical activity to a digital signal indicative of cardiac electrical activity, and detecting R-waves by comparing the digital signal indicative of cardiac electrical activity to a fixed detection threshold to thereby detect threshold crossings that corresponds to R-waves. The method further includes selectively adjusting a gain applied to the digital signal indicative of cardiac electrical activity to thereby selectively adjust a sensitivity associated with the detecting R-waves, while maintaining the fixed detection threshold.

24 Claims, 6 Drawing Sheets

(56) References Cited

U.S. PATENT DOCUMENTS

| | | | |
|---|---|---|---|
| 7,403,813 B1 | 7/2008 | Farazi et al. | |
| 7,756,570 B1 | 7/2010 | Bornzin | |
| 9,636,505 B2 | 5/2017 | Sanghera et al. | |
| 2004/0062326 A1* | 4/2004 | Burke | H03G 3/3036 |
| | | | 375/345 |
| 2009/0082691 A1* | 3/2009 | Denison | A61B 5/374 |
| | | | 600/544 |
| 2012/0104235 A1* | 5/2012 | Sumi | H04N 5/3575 |
| | | | 250/208.1 |
| 2015/0305641 A1* | 10/2015 | Stadler | A61B 5/363 |
| | | | 600/510 |
| 2018/0234059 A1 | 8/2018 | Rao et al. | |
| 2019/0380610 A1* | 12/2019 | Bornzin | A61B 5/0432 |

OTHER PUBLICATIONS

Response to Communication pursuant to Rules 161(1) and 162 EPC dated Jun. 10, 2021, European Patent Application No. 19783781.8-1113.

Communicationpursuant to Rules 161(1) and 162 EPC dated Jun. 1, 2021, European Patent Application No. 19783781.3-1113.

* cited by examiner

DYNAMIC CONTROL OF SENSITIVITY ASSOCIATED WITH DETECTING R-WAVES

FIELD OF INVENTION

Embodiments described herein relates to methods, devices, and systems that detect R-waves within a signal indicative of cardiac electrical activity, such as an electrocardiogram (ECG) or an intracardiac electrogram (IEGM).

BACKGROUND

An implantable cardiac device, which can also be referred to more generally as an implantable medical device (IMD), often includes electrodes that enable the IMD to sense an electrocardiogram (ECG) or an intracardiac electrogram (IEGM), which can be referred to collectively as an ECG/IEGM, or more generally as a signal indicative of cardiac electrical activity. FIG. 1 is an idealized drawing of a portion of an ECG/IEGM signal 102 (which can also be referred to as an ECG/IEGM waveform 102) that can be obtained using electrodes. One or more of the electrodes can be elements of a cardiac lead, for example, where such electrodes can be implanted within a patient's heart. It is also possible that electrodes be sub-cutaneous electrodes that are implanted external to a patient's heart. For another example, where the IMD is a leadless pacemaker, the electrodes can be located within, on, or near a housing of the leadless pacemaker. These are just a few examples of the type of electrodes that can be used to sense an ECG/IEGM.

Referring to FIG. 1, each cycle of the ECG/IEGM signal 102 is shown as including a P wave, a QRS complex (including Q, R and S waves), a T wave and a U wave. The P wave is caused by depolarization of the atria. This is followed by an atrial contraction, during which expulsion of blood from the atrium results in further filling of the ventricle. Ventricular depolarization, indicated by the QRS complex, initiates contraction of the ventricles resulting in a rise in ventricular pressure until it exceeds the pulmonary and aortic diastolic blood pressures to result in forward flow as the blood is ejected from the ventricles. The Q, R, and S waves occur in rapid succession, and reflect a single event, and thus are usually considered together as the QRS complex. The Q wave is any downward deflection after the P wave. An R wave follows as an upward deflection, and the S wave is any downward deflection after the R wave. Ventricular repolarization occurs thereafter, as indicated by the T wave and this is associated with the onset of ventricular relaxation in which forward flow stops from the ventricles into the aorta and pulmonary arteries. Thereafter, the pressure in the ventricles falls below that in the atria at which time the mitral and tricuspid valves open to begin to passively fill the ventricles during diastole. Also shown in the exemplary ECG signal 102 is a U wave, which may not always be observed as a result of its small size, and which is thought to represent repolarization of the Purkinje fibers.

Also shown in FIG. 1 are various different intervals and segments that can be measured from an ECG/IEGM signal, such as the ECG/IEGM signal 102. These various intervals and segments are examples of features of an ECG/IEGM signal. These include the PR interval, the QT interval, the RR interval, the PR segment, and the ST segment. The PR interval, which is sometimes referred to as the PQ interval, is the period that extends from the beginning of the P wave (the onset of atrial depolarization) until the beginning of the QRS complex (the onset of ventricular depolarization), and is normally between about 120 and 200 milliseconds (ms) in duration. The length and/or variability of the PR interval can be used to monitor for certain medical conditions, such as, but not limited to, heart block and pericarditis. The QT interval, which is the period that extends from the beginning of the Q wave until the end of the T wave, represents electrical depolarization and repolarization of the ventricles. A lengthened QT interval is a marker for the potential of ventricular tachyarrhythmias like torsades de pointes and a risk factor for sudden death. The RR interval is the period between R waves, or more generally, between QRS complexes, and is indicative of the heart rate (HR). For example, HR in beats per minute (bpm) can be determined by measuring a plurality of RR intervals, calculating an average RR interval, and dividing the number sixty (60) by the average RR interval. RR intervals can also be used to measure heart rate variability (HRV), which is the physiological phenomenon of variation in the time interval between heartbeats, which has been shown to be predictor of mortality after myocardial infarction. Additionally, a low HRV is believed to be an indicator of other conditions, such as congestive heart failure and diabetic neuropathy. HRV can be determined by calculating a measure of variance in RR intervals, such as, but not limited to, by calculating the standard deviation (SD), the root mean square of successive differences (RMSSD), or the standard deviation of successive differences (SDSD) of a plurality of consecutive RR intervals. The PR segment is the period that extends from the end of the P wave to the beginning of the QRS complex. PR segment abnormalities can be indicative of pericarditis or atrial ischemia. The ST segment is the period that extends from the end of the S wave (or the end of the QRS complex) to the beginning of the T wave, and is normally between about 80 and 120 ms in duration. A normal ST segment has a slight upward concavity. A flat, downsloping, or depressed ST segments, may indicate coronary ischemia. ST elevation may indicate transmural myocardial infarction. ST depression may be associated with subendocardial myocardial infarction, hypokalemia, or *digitalis* toxicity.

A fundamental operation of many types of IMDs is the ability to measure RR intervals, which enables the IMD to calculate HR and HRV, e.g., in the manners described above. Depending upon the specific type of IMD, RR intervals (and/or measures of HR calculated therefrom) can be used to monitor for arrhythmias, respond to arrhythmias, and/or the like. In order to measure RR intervals from an ECG/IEGM, an IMD should detect R-waves within an ECG/IEGM signal.

Conventionally, R-waves are detected by comparing the amplitude of an ECG/IEGM signal to a detection threshold, and detecting R-waves in response to a threshold crossing in a particular direction. Such a technique can be appreciated from FIG. 2, which shows how the ECG/IEGM signal 102 can be compared to a detection threshold 204 represented by a dashed line. As can also be appreciated from FIG. 2, an RR interval can be determined by measuring the interval between successive crossings of the detection threshold 204 in a particular direction. In other words, when the ECG/IEGM crosses the detection threshold 204 the interval between consecutive crossings (in the same direction) can be recorded and used to determine the RR interval. This interval can be used in various manners, including to make therapy decisions within the IMD.

When measuring RR intervals, or more generally detecting R-waves, it is important for the IMD to not mistaken one or more other morphological features of an ECG/IEGM signal as an R-wave. For example, it is important that an IMD not mistaken a T-wave for an R-wave, which can lead to the IMD mistakenly detecting very short RR intervals (or a very high HR). To avoid this, some IMDs adjust the amplitude of the detection threshold over time in relation to R-waves. This adjusting of the detection threshold is sometimes called automatic sensitivity control (ASC). The ASC feature of an IMD may, for example, automatically measure peak amplitudes of an ECG/IEGM signal and adapt the detection threshold (e.g., 204 in FIG. 2) automatically. For a more specific example, after every detection threshold crossing indicative of an R-wave, a peak of the ECG/IEGM signal may be measured, and the detection threshold can be adjusted based on how close the peak is to the detection threshold. This may involve, for example, decreasing the detection threshold if the peak is much greater than the detection threshold, and increasing the detection threshold if the peak is only slightly greater than the detection threshold.

SUMMARY

Certain embodiments of the present technology relate to implantable medical devices (IMDs), and methods for use therewith, for dynamically controlling sensitivity associated with detecting R-waves without dynamically adjusting a detection threshold, and more specifically, while maintaining a fixed detection threshold. Such a method can include sensing an analog signal indicative of cardiac electrical activity, converting the analog signal indicative of cardiac electrical activity to a digital signal indicative of cardiac electrical activity, and detecting R-waves by comparing the digital signal indicative of cardiac electrical activity to a fixed detection threshold to thereby detect threshold crossings that corresponds to R-waves. The fixed detection threshold can be specified, e.g., during manufacture of an IMD that implements the method, during calibration of an IMD that implements the method, prior to implantation of an IMD that implements the method, or after implantation of the IMD that implements the method. The method further includes selectively adjusting a gain applied to the digital signal indicative of cardiac electrical activity to thereby selectively adjust a sensitivity associated with the detecting R-waves, while maintaining the fixed detection threshold.

In accordance with certain embodiments, the analog signal indicative of cardiac electrical activity is converted to the digital signal indicative of cardiac electrical activity is performed using an N-bit analog-to-digital converter (ADC) and a multiplier. The ADC accepts the analog signal indicative of cardiac electrical activity and outputs an N-bit digital signal. A course gain factor specifies which M-bits, of the N-bit digital signal output by the N-bit ADC, are provided to the multiplier, where M<N. In accordance with certain embodiments, the gain applied to the digital signal indicative of cardiac electrical activity is selectively adjusted, at least in part, by selectively adjusting the course gain factor. Additionally, or alternatively, a fine gain factor specifies a value that the M-bits, provided to the multiplier, are multiplied by to produce the digital signal indicative of cardiac electrical activity that is compared to the fixed detection threshold to detect R-waves. In accordance with certain embodiments, the gain applied to the digital signal indicative of cardiac electrical activity is selectively adjusted, at least in part, by selectively adjusting the fine gain factor.

Certain methods involve detecting peak amplitudes of the digital signal indicative of cardiac electrical activity, by detecting a peak amplitude of the digital signal indicative of cardiac electrical activity within a window following a threshold crossing, each time the comparing results in a threshold crossing that corresponds to an R-wave. In such embodiments, the selectively adjusting the fine gain factor can be based on the peak amplitudes of the digital signal indicative of cardiac electrical activity. This can involve, for example, adjusting the fine gain factor in response to the peak amplitude (of the digital signal indicative of cardiac electrical activity) being outside a specified range, and not adjusting the fine gain factor in response to the peak amplitude (of the digital signal indicative of cardiac electrical activity) being within the specified range. The adjusting the fine gain factor (in response to the peak amplitude of the digital signal indicative of cardiac electrical activity, being outside the specified range) can involve decreasing the fine gain factor in response to the peak amplitude (of the digital signal indicative of cardiac electrical activity) being above the specified range, and increasing the fine gain factor in response to the peak amplitude (of the digital signal indicative of cardiac electrical activity) being below the specified range.

An IMD that implements an above summarized method can, for example, measure RR intervals based on detected R-waves, monitor for one or more types of arrhythmias based on the RR intervals, and triggering an action in response to an arrhythmia being detected. Depending upon the specific arrhythmia detected, and the specific IMD, the action can involve stimulation therapy, including pacing, cardioversion and/or defibrillation stimulation, but is not limited thereto.

An IMD according to an embodiment of the present technology can include a plurality of electrodes, a sense amplifier, an analog-to-digital converter (ADC), adjustable gain circuitry downstream of the ADC, a comparator downstream of the adjustable gain circuitry, and a controller. The sense amplifier, which can be coupled to a pair of the electrodes, is configured to output an analog signal indicative of cardiac electrical activity, such as an ECG/IEGM signal. The ADC is configured to convert the analog signal indicative of cardiac electrical activity to a digital signal indicative of cardiac electrical activity. The adjustable gain circuitry is configured to adjust a gain applied to the digital signal indicative of cardiac electrical activity. The comparator is configured to detect R-waves by comparing the digital signal indicative of cardiac electrical activity to a fixed detection threshold to thereby detect threshold crossings that corresponds to R-waves. The controller is configured to selectively adjust the gain applied by the adjustable gain circuitry to thereby selectively adjust a sensitivity associated with the comparator detecting R-waves by detecting threshold crossings that corresponds to R-waves.

In accordance with certain embodiments, the ADC comprise an N-bit ADC, and the adjustable gain circuitry comprises an M-bit selector downstream of the N-bit ADC and a multiplier downstream of the M-bit selector. The M-bit selector can be configured to select which M-bits of an N-bit digital signal output by the N-bit ADC is provided to the multiplier, where M<N. The multiplier can be configured to multiplying the M-bits, selected by the M-bit selector, by a value provided to the multiplier by the controller. In accordance with certain embodiments, the controller is configured to perform one or more course gain adjustments by changing which M-bits of the N-bit digital signal output by the N-bit ADC is provided to the multiplier. Additionally, or alternatively, the controller can be configured to perform one or more fine gain adjustments by selectively changing the value, provided to the multiplier, that is multiplied by the M-bits selected by the M-bit selector. It would also be possible to not have an M-bit selector between the ADC and the multiplier, in which case, the adjustable gain circuitry can comprise the multiplier downstream of the ADC, and the controller can be configured to adjust the gain applied by the adjustable gain circuitry by changing a value that is provided to the multiplier to multiply by a digital signal output by the ADC.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

As noted above in the Background, some IMDs use automatic sensitivity control (ASC) to adjust a detection threshold that is used for detecting R-waves (and RR intervals). In general, with conventional ASC the amplitude of the detection threshold is varied and the amplitude of a gain applied to an ECG/IEGM signal (that is being compared to the detection threshold) is not adjusted. This is mostly due to the complexity involved with supporting a wide range and resolution of gain for an ECG/IEGM sense amplifier.

In accordance with certain embodiments of the present technology, rather than adjusting the threshold that is used for detecting R-waves (and RR intervals), one or more gains (which adjust the amplitude of the ECG/IEGM signal) is/are adjusted, and a fixed detection threshold is maintained. This provides for some circuit simplification and reduced complexity. Further, where an IMD already has an adjustable gain capability to allow for patient variability, such embodiments of the present technology can take advantage of a capability already built into the IMD.

Figure 1:
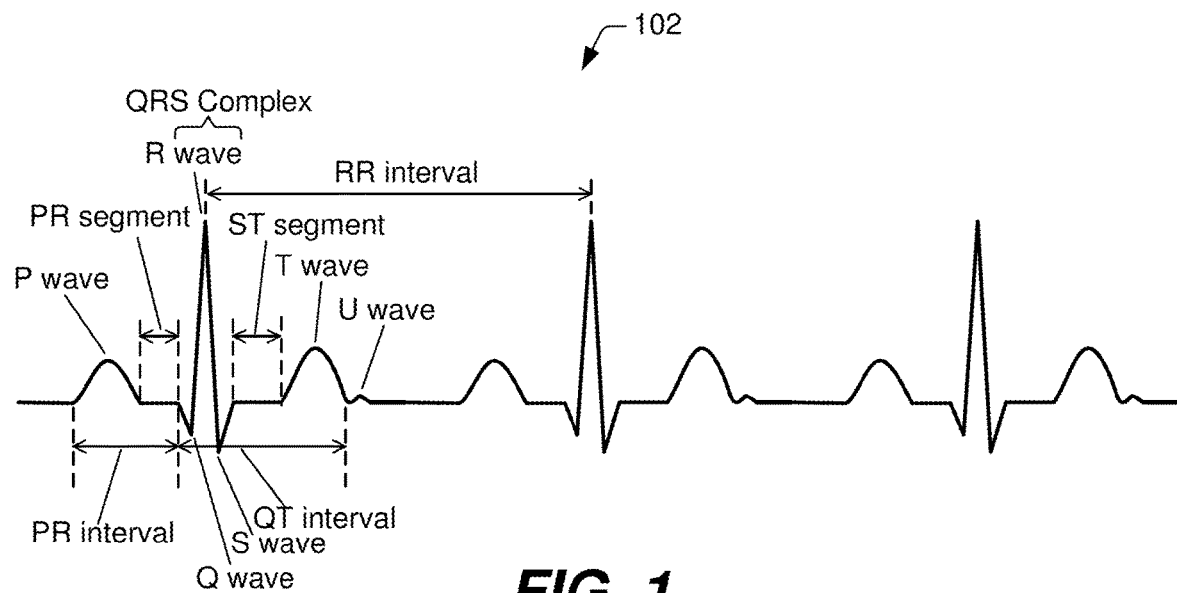
FIG. 1 is an idealized drawing of a portion of an ECG/IEGM signal indicative of cardiac electrical activity.
Figure 2:
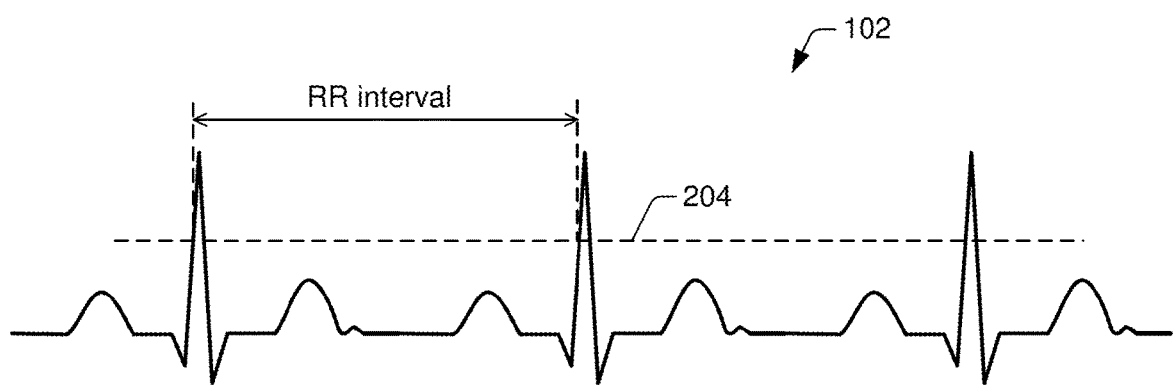
FIG. 2 illustrates how the ECG/IEGM signal introduced in FIG. 1 can be compared to a threshold to detect R-waves and RR intervals.
Figure 3:
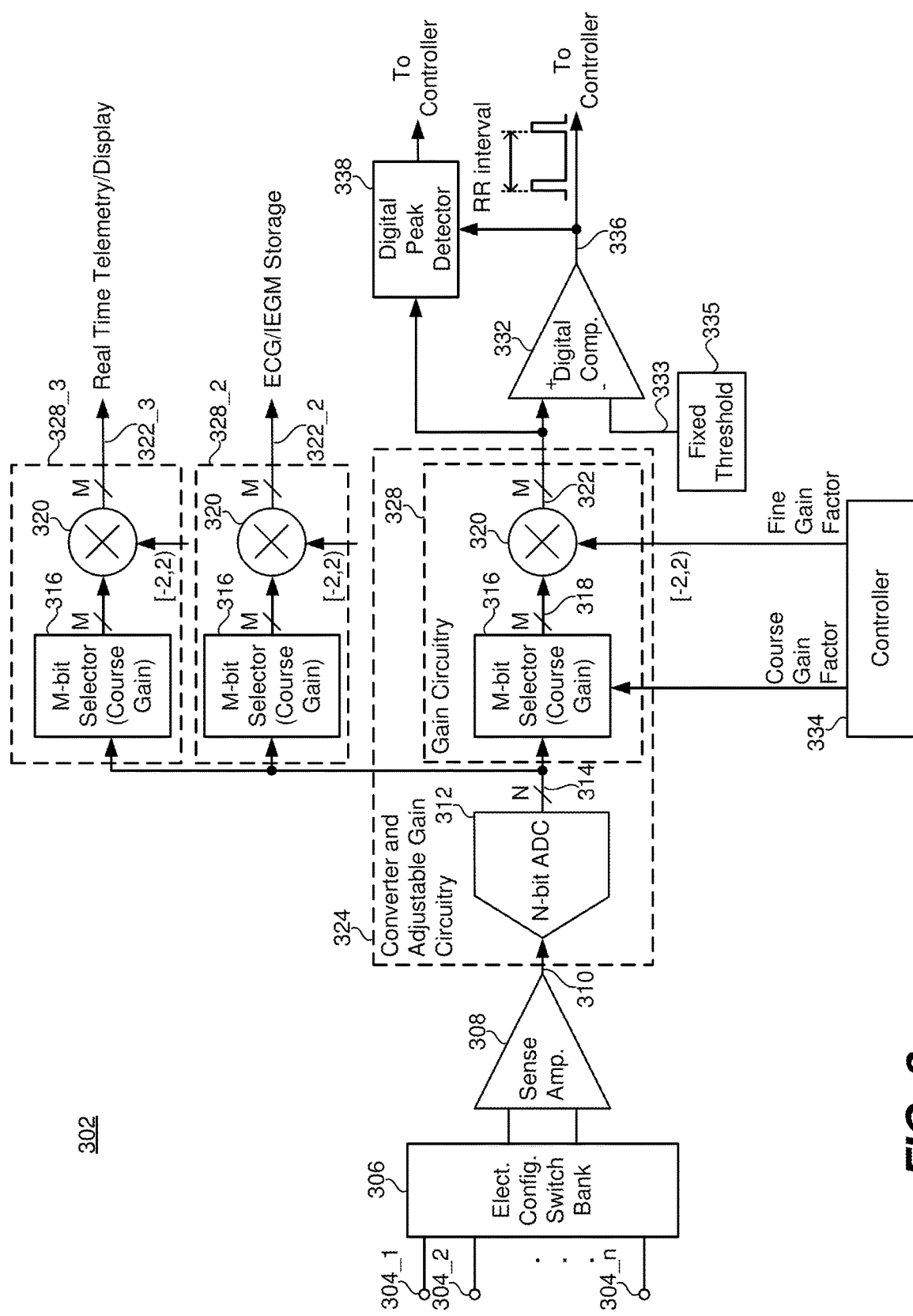
FIG. 3 is a high level block diagram of a portion of IMD that can control sensitivity associated with the detecting R-waves while maintaining the fixed detection threshold.

FIG. 3 is a high level block diagram of circuitry that can be used to detect R-waves, and more specifically, can control sensitivity associated with the detecting R-waves while maintaining a fixed detection threshold. Referring to FIG. 3, the IMD is shown as including a plurality of electrodes 304_1, 304_2, . . . 304_N, which can be referred to collectively as the electrodes 304, or individually as an electrode 304. An electrode configuration switch bank 306 is used to select which pair of the electrodes 304 is coupled to a sense amplifier 308. The sense amplifier 308 outputs an analog signal indicative of cardiac electrical activity, e.g., an ECG/IEGM signal similar to the one shown in FIG. 1. If an IMD includes only a pair of electrodes, as is the case with some leadless pacemakers, there is no need for the switch bank 306. In other words, if an IMD includes only two electrodes, those two electrodes can always be directly coupled to the sense amplifier 308.

Downstream of the sense amplifier 308 is an N-bit analog-to-digital converter (ADC) 312 that converts the analog signal indicative of cardiac electrical activity, which is output by the sense amplifier 308, to a digital signal indicative of cardiac electrical activity. Downstream of the ADC 312 is gain circuitry 328 that can be used to adjust a gain applied to the digital signal indicative of cardiac electrical activity, which is output by the ADC 312. In accordance with certain embodiments, the gain circuitry 328 includes both course gain circuitry and fine gain circuitry. In the embodiment shown in FIG. 3, the course gain circuitry is an M-bit selector 316, and the fine gain circuitry is a multiplier 320. Both the M-bit selector 316 and the multiplier 320 can be controlled by a controller 334.

Figure 4:
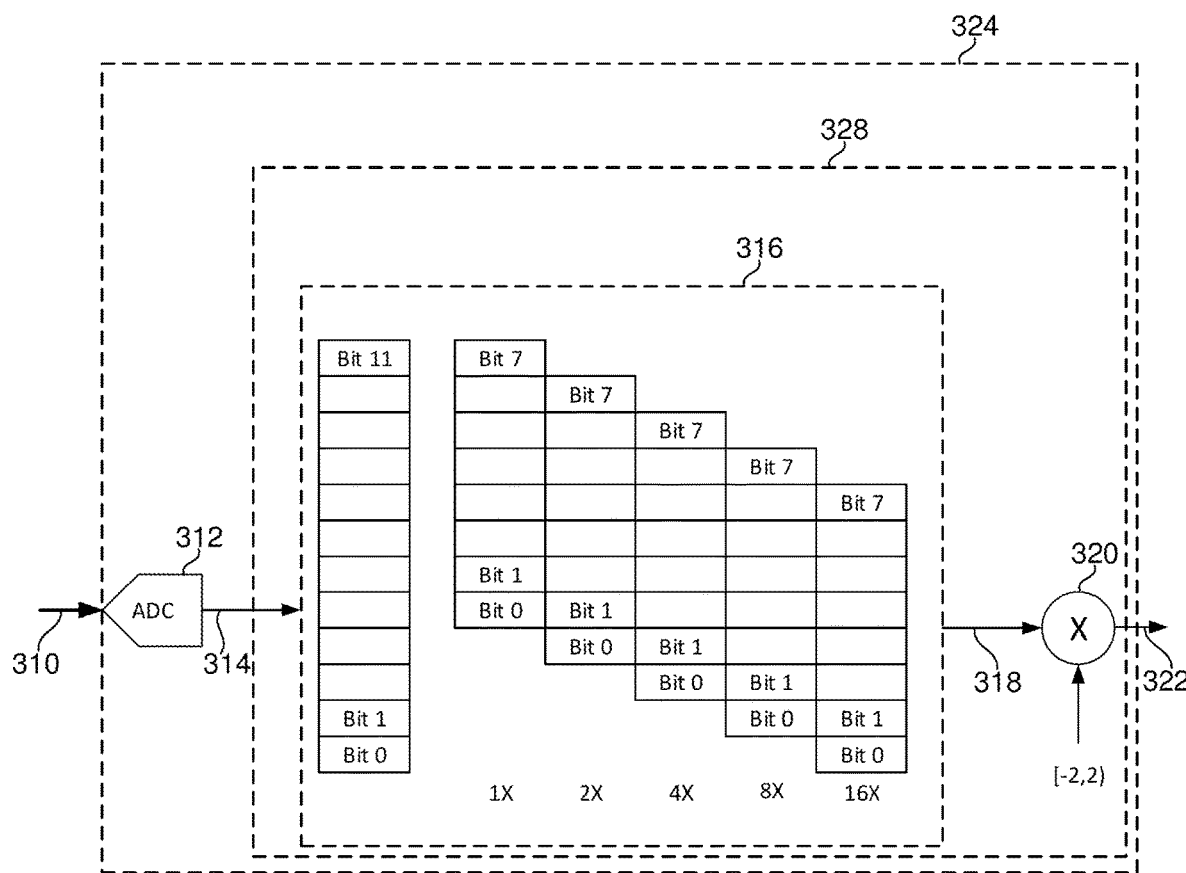
FIG. 4 pictorially illustrates how an M-bit selector, introduced in FIG. 3, can be used to apply course gain adjustments to a digital signal indicative of cardiac electrical activity.

The M-bit selector 316, under the control of the controller 334, selects which M-bits of the N-bit digital signal digital signal (output by the N-bit ADC) is provided to the multiplier, where M<N. In this manner, the M-bit selector either applies 1× gain, 2× gain, 4× gain, 8× gain, etc., to the digital signal indicative of cardiac electrical activity. For example, assume that N=12, and M=8, meaning the ADC 312 is a 12-bit ADC and the M-bit selector 316 is an 8-bit selector. Also assume that the least significant bit (LSB) is the $0^{th}$ bit and the most significant bit (MSB) is the 11th bit of the 12-bit output of the ADC 312. Continuing with this example: 1× gain can be applied by selecting bits 4 through 11 of the 12-bit output of the ADC 312; 2× gain can be applied by selecting bits 3 through 10 of the 12-bit output of the ADC 312; 4× gain can be applied by selecting bits 2 through 9 of the 12-bit output of the ADC 312; 8× gain can be applied by selecting bits 1 through 8 of the 12-bit output of the ADC 312; and 16× gain can be applied by selecting bits 0 through 7 of the 12-bit output of the ADC 312. This is pictorially illustrated in FIG. 4. In accordance with an embodiment, the M-bit selector is implemented using an M-bit register that accepts M-bits, but only output a selected N-bits of the M-bits. For a more specific example, the M-bit selector 316 can be implemented using an M-bit shift register and hardware that can apply a gain by selectively and appropriately shifting up to M−N bits. M−N bits (for 16× gain), M−N−1 bits (for 8× gain), M−N−2 bits (for 4× gain), etc. Again assume that N=12, and M=8, meaning the ADC 312 is a 12-bit ADC and the M-bit selector 316 is an 8-bit selector. In order to apply a 16× gain, the 12-bit output of the ADC can be loaded into the M-bit shift register, and hardware can be used to arithmetically shift the data by M−N bits (i.e., by 12−8=4 bits); in order to apply a 8× gain, the 12-bit output of the ADC can be loaded into the M-bit shift register and hardware can be used to arithmetically shift the data by M−N−1 bits (i.e., by 12−8−1=3 bits); in order to apply a 4× gain, the 12-bit output of the ADC can be loaded into the M-bit shift register and hardware can be used to arithmetically shift the data by M−N−2 bits (i.e., by 12−8−2=2 bits); etc. This can be accomplished by always taking the N most significant bits from M after the arithmetic shift. These are all binary point shifts, so only factors of 2× gain are permissible with such an implementation. Other ways of implementing the M-bit selector are also possible and within the scope of the embodiments disclosed herein.

Referring again to FIG. 3, the multiplier 320 multiplies the M-bits (selected by the M-bit selector) by a value provided to the multiplier 320 by the controller 334. The value that the controller 334 provides to the multiplier 320 can be referred to as a "fine gain factor." By contrast, a "course gain factor" that is generated by the controller 334 specifies which M-bits (of the N-bits output by the ADC 312) are provided to the multiplier 320. In accordance with certain embodiments, the fine gain factor can be a value between negative two inclusive, and positive two exclusive. In other words, the fine gain factors can be within the range of [−2,2). Other variations are also possible and within the scope of the embodiments described herein.

The signal 322 output by the multiplier 320, which is a digital signal indicative of cardiac electrical activity 322 (to which gain has been applied) is provided to a comparator 332. The comparator 332 compares the digital signal indicative of cardiac electrical activity 322 to a fixed detection threshold 333, a value for which can be stored in a register 335, or the like. In the embodiments shown, the digital signal indicative of cardiac electrical activity 322 is provided to the positive (+) terminal of the comparator 332, and the fixed threshold 333 is provided to the negative (−) terminal of the comparator 332. In such a configuration, the signal 336 output by the comparator 332 will be go HIGH whenever the digital signal indicative of cardiac electrical activity 322 (to which gain has been applied) exceeds the fixed detection threshold 333, and will go LOW whenever the digital signal indicative of cardiac electrical activity 322 (to which gain has been applied) is below the fixed threshold 333.

The controller 334 can perform course gain adjustments by changing which M-bits (of the N-bit digital signal) output by the N-bit ADC 312 is provided to the multiplier 320. The controller 334 can perform fine gain adjustments by selectively changing the value, provided to the multiplier 320, that is multiplied by the M-bits selected by the M-bit selector 316. In accordance with certain embodiments, an appropriate course gain factor is selected once, e.g., during calibration, but the fine gain factor is dynamically adjusted over time by the controller 334 to provide automatic sensitivity control (ASC) after the IMD including the circuitry has been implanted within a patient. In other embodiments, both the course gain factor and the fine gain factor are dynamically adjusted by the controller 334 over time to provide automatic sensitivity control (ASC) after the IMD including the circuitry is implanted within a patient. In FIG. 3, the multiplier 320 is shown as being downstream of the M-bit selector 316 within the gain circuitry 328. In alternatively embodiments the order of the M-bit selector 316 and the multiplier 320 are reversed such that the M-bit selector 316 is downstream of the multiplier 320, in which case a fine gain adjustment can be performed prior to a course gain adjustment.

The ADC 312 and the gain circuitry 328 can be referred to collectively as converter and adjustable gain circuitry 324. The converter and adjustable gain circuitry 324 can include the ADC 312, the M-bit selector 316, and the multiplier 320. In an alternative embodiment, the M-bit selector 316 can be eliminated, and the converter and adjustable gain circuitry 324 can include the ADC 312 and the multiplier 320. In another alternative embodiment, the multiplier 320 can be eliminated, and the converter and adjustable gain circuitry 324 can include the ADC 312 and the M-bit selector 316. For much of the remaining description is will be assumed that the converter and adjustable gain circuitry 324 includes the ADC 312, the M-bit selector 316, and the multiplier 320. As noted above, the order of the M-bit selector 316 and the multiplier 320 can be reversed such that the multiplier 320 follows the ADC 312, and the M-bit selector follows the multiplier 320. However, for much of the remaining description is will be assumed that the M-bit selector 316 follows the ADC 312, and the multiplier 320 follows the M-bit selector 316, as is shown in FIG. 3. Nevertheless, embodiments of the present technology also cover the alternative ordering of the multiplier 320 and the M-bit selector 316.

Details are now provided as to how adjustments can be performed to the gain applied to digital signal indicative of cardiac electrical activity. Still referring to FIG. 3, the digital signal 322 (indicative of cardiac electrical activity) that is output by the gain circuitry 328, in addition to be provided to the digital comparator 332, is also shown as being provided to a digital peak detector 338. The signal 336 output by the comparator 332 is used to trigger the peak detector 338 to detect a peak amplitude of the digital signal 322 (indicative of cardiac electrical activity) within a temporal window following a threshold crossing (in a specific direction). Such a detected peak amplitude should correspond to a peak amplitude of an R-wave. In accordance with certain embodiments, the gain (e.g., the fine gain factor) is increased if the peak amplitude is much greater than the fixed threshold, and the gain is decreased if the peak amplitude is only slightly greater than the fixed threshold. There are various ways to achieve such functionality. For example, in an embodiment, the gain (e.g., the fine gain factor) is increased if the peak amplitude is more than X percent (e.g., more than 50%) greater than the fixed threshold, the gain is decreased if the peak amplitude is less than Y percent (e.g., 20%) greater than the fixed threshold, and the gain is not adjusted if the peak amplitude is between X and Y percent (e.g., between 20% and 50%) greater than the fixed threshold. Other variations are also possible and within the embodiments of the present technology. For example, an amount by which the gain is increased or decreased can depend upon a magnitude of a difference between the peak amplitude and the fixed threshold, wherein the greater the magnitude the greater the adjustment.

In FIG. 3, the signal 336 output by the comparator 332, which is indicative of R-wave detections, is shown as being provided to the controller 334. This enables the controller 334 to determine RR intervals as well as HR, HRV, and the like. For example, the controller 334 can determine RR intervals by determining the time between successive leading edges of the pulses in the signal 336 output by the comparator 332. The controller 334 can determine HR in beats per minute (bpm) by determining an average of a plurality of the RR intervals, and dividing the number sixty (60) by the average RR interval. The controller 334 can determine HRV by calculating a measure of variance in RR intervals, such as, but not limited to, by calculating the standard deviation (SD), the root mean square of successive differences (RMSSD), or the standard deviation of successive differences (SDSD) of a plurality of consecutive RR intervals.

Additional instances of the gain circuitry 328 are also shown in FIG. 3, with the additional instances labeled 328_2 and 328_3. While the gain circuitry 328 applies a gain to the signal 314 to produce the gain adjusted signal 322, which is used to detect R-waves, RR intervals, etc., the signal 314 can also be provided to the gain circuitry 328_2 and 328_3, as shown in FIG. 3. The gain circuitry 328_2 can be used to apply an appropriate gain such that a gain adjusted signal 322_2 output therefrom is within an appropriate amplitude range used to store an ECG/IEGM signal, or segments thereof, in memory for later uploading and/or analysis. The gain circuitry 328_3 can be used to apply an appropriate gain such that a gain adjusted signal 322_3 output therefrom is within an appropriate amplitude range used to perform real time telemetry (and potentially real time display) of an ECG/IEGM signal. More generally, the circuitry 302 can include multiple gain channels that are used to apply various different adjustable gains to a digital signal indicative of cardiac electrical activity, which signal can also be referred to as an ECG/IEGM signal.

Each instance of the gain circuitry 328 shown in FIG. 3 was shown as including an M-bit selector 316 (used to perform course gain adjustments) and a multiplier 320 (used to perform fine gain adjustments). As noted above, the order of the M-bit selector 316 and the multiplier 320 can be reversed, such that the multiplier 320 is upstream of the M-bit selector. In alternative embodiments, one or more instances of the gain circuitry 328 (e.g., potentially all instances of the gain circuitry 328) includes a multiplier 320 but does not include an M-bit selector 316. In such an embodiment, a digital signal output by the ADC 312 can be provided directly to the multiplier 320, and the controller can adjust the gain applied to the digital signal indicative of cardiac electrical activity by changing the value that the controller provides to the multiplier 320. Where there are multiple instances of gain circuitry 328, and thus multiple instances of the multiplier 320, the controller 334 can provide different values to the different multipliers 320 to apply different gains to generate multiple digital signals indicative of cardiac electrical activity.

In the embodiments described above with reference to FIG. 3, gain adjustments are performed in the digital domain, i.e., after the sensed analog signal indicative of cardiac electrical activity is converted to a digital signal indicative of cardiac electrical activity by the ADC 312. This is beneficial because gain adjustments performed in the digital domain do not cause artefacts that often occur where gain adjustments are performed in the analog domain. Such artefacts, when they occur, can result in false detections of R-waves, i.e., in false positives. By performing the gain adjustments in the digital domain, such artefacts are avoided, and thus, the gain adjustments do not increase in the likelihood that false detections of R-waves will occur.

The circuitry 302 shown in FIG. 3 can be part of a pacemaker and/or implantable cardioverter defibrillator (ICD) to which are connected leads having electrodes, or part of a leadless pacemaker, or part of an implantable cardiac monitor that does not provide any therapy, but is not limited thereto. An exemplary IMD in which such circuitry 302 can be included is discussed below with reference to FIGS. 6 and 7.

Figure 5:
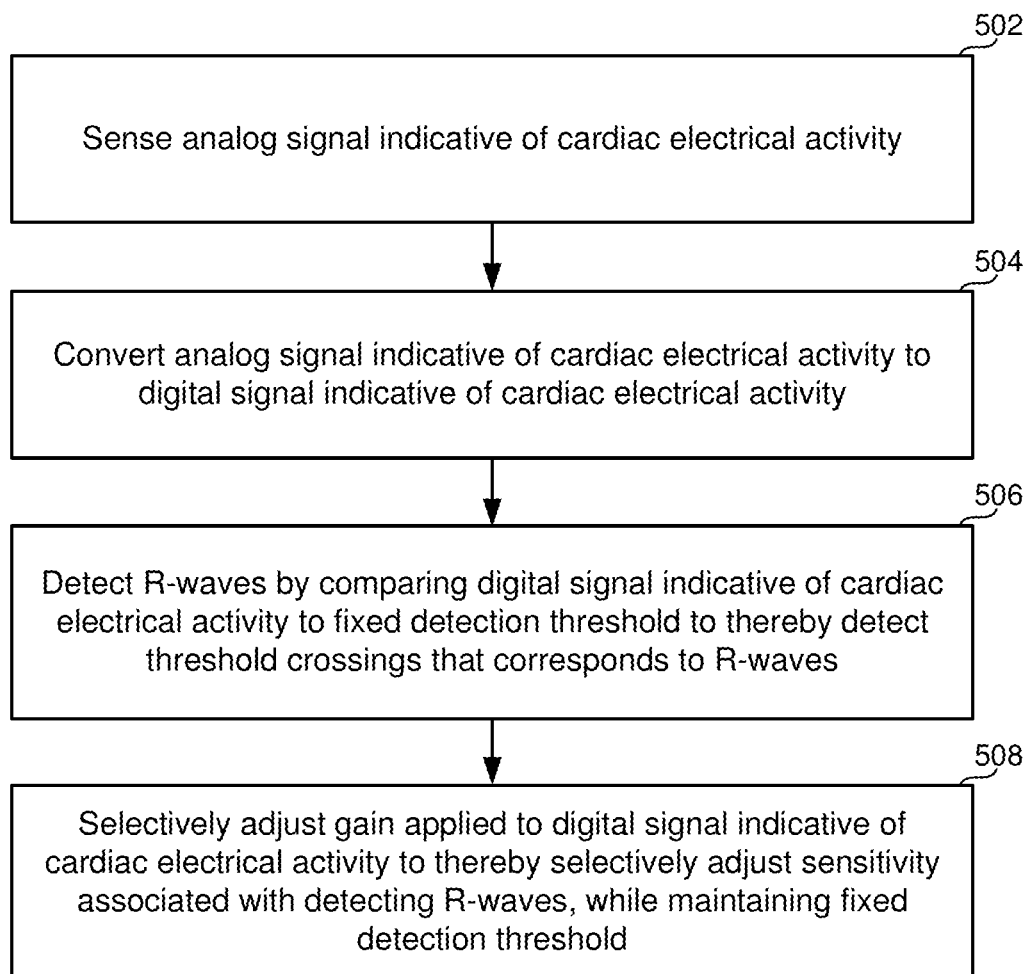
FIG. 5 is a high level flow diagram that is used to summarize methods for dynamically controlling sensitivity associated with detecting R-waves, in accordance with various embodiments of the present technology.

The high level flow diagram of FIG. 5 will now be used to summarize methods for dynamically controlling sensitivity associated with detecting R-waves, in accordance with various embodiments of the present technology. Referring to FIG. 5, step 502 involves sensing an analog signal indicative of cardiac electrical activity. Step 504 involves converting the analog signal indicative of cardiac electrical activity to a digital signal indicative of cardiac electrical activity. Step 506 involves detecting R-waves by comparing the digital signal indicative of cardiac electrical activity to a fixed detection threshold to thereby detect threshold crossings that corresponds to R-waves. Step 508 involves selectively adjusting a gain applied to the digital signal indicative of cardiac electrical activity to thereby selectively adjust a sensitivity associated with the detecting R-waves, while maintaining the fixed detection threshold.

Step 502 can be performed, e.g., using a pair of electrodes (304 in FIG. 3) and a sense amplifier (308 in FIG. 3), which are used to sense an ECG/IEGM signal.

Step 504 can be performed, e.g., using an N-bit ADC (e.g., 312 in FIG. 3) that accepts the analog signal indicative of cardiac electrical activity and outputs an N-bit digital signal. In accordance with certain embodiments, a course gain factor specifies which M-bits, of the N-bit digital signal output by the N-bit ADC, are used when comparing the digital signal indicative of cardiac electrical activity to the fixed detection threshold to thereby detect threshold crossings that corresponds to R-waves, where M<N. Additionally, or alternatively, a fine gain factor can specify a value that the M-bits, provided to the multiplier, are multiplied by to produce the digital signal indicative of cardiac electrical activity that is compared to the fixed detection threshold to detect R-waves. In certain embodiments, the selectively adjusting the gain applied to the digital signal indicative of cardiac electrical activity is performed at step 508 by selectively adjusting the course gain factor. Additionally, or alternatively, step 508 can be performed by selectively adjusting the fine gain factor.

In accordance with certain embodiments, each time there is a threshold crossing in a particular direction (that is indicative of an R-wave detection), a peak amplitude of the digital signal indicative of cardiac electrical activity is detected within a window following the threshold crossing. In such embodiments, the fine gain factor can be selectively adjusted based on the peak amplitudes of the digital signal indicative of cardiac electrical activity. In certain embodiments this involves a controller (e.g., 334 in FIG. 3) changing a value that it provides to a multiplier (e.g., 320 in FIG. 3).

Selectively adjusting the fine gain factor, in accordance with certain embodiments, involves adjusting the fine gain factor in response to a peak amplitude (of the digital signal indicative of cardiac electrical activity) being outside a specified range, and not adjusting the fine gain factor in response to the peak amplitude (of the digital signal indicative of cardiac electrical activity) being within the specified range. More specifically, this can involve decreasing the fine gain factor in response to the peak amplitude (of the digital signal indicative of cardiac electrical activity) being above the specified range, and increasing the fine gain factor in response to the peak amplitude (of the digital signal indicative of cardiac electrical activity) being below the specified range. Other variations are also possible and within the scope of the embodiments described herein.

An exemplary IMD that can include the circuitry 302 discussed above with reference to FIG. 3, and that can be used to perform the methods summarized with reference to FIG. 5, will now be discussed below with reference to FIGS. 6 and 7.

Exemplary IMD

Figure 6:
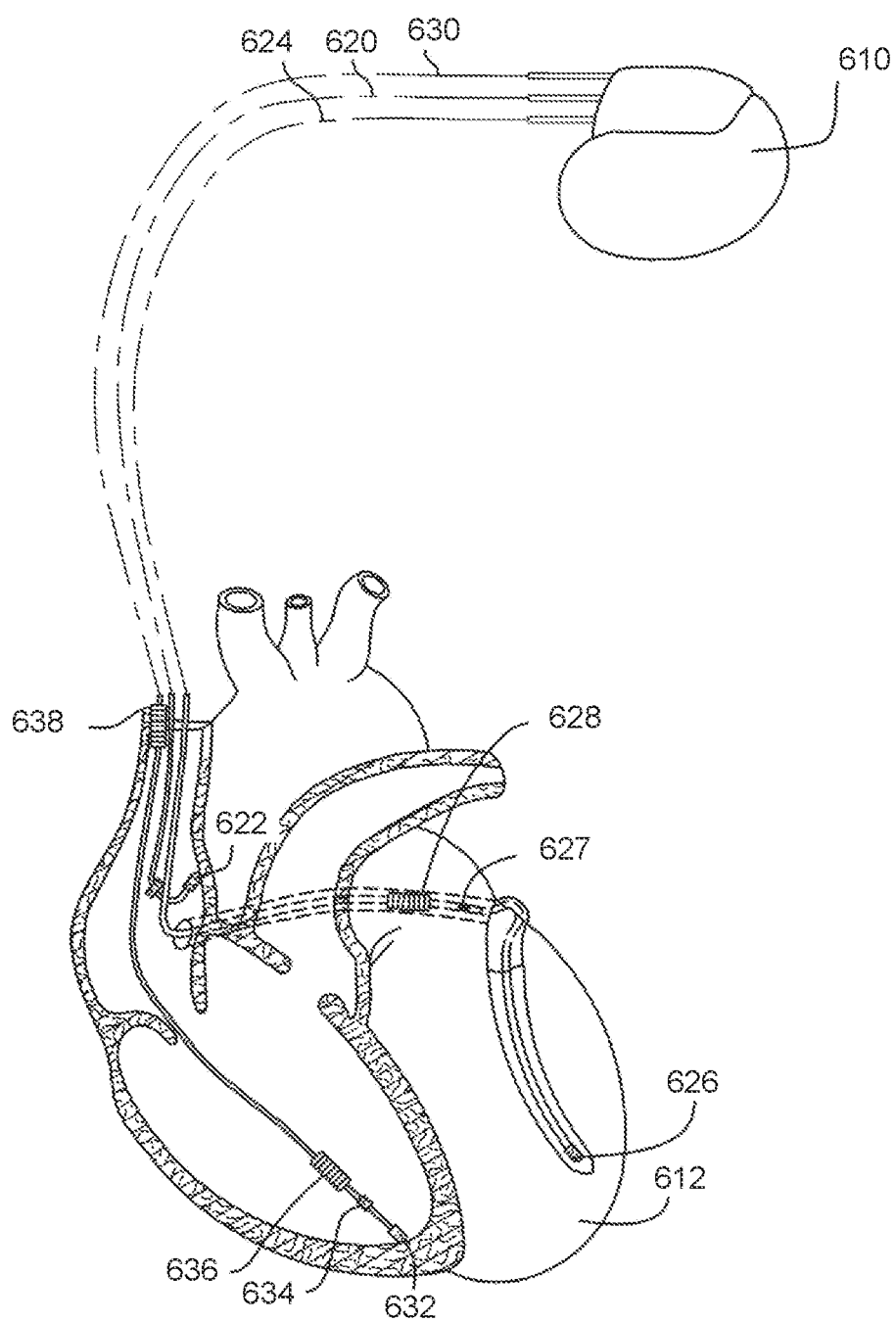
FIG. 6 is an exemplary IMD within which embodiments of the present technology may be implemented.

Referring to FIG. 6, an exemplary IMD 610 (also referred to as a pacing device, a pacing apparatus, a stimulation device, an implantable device or simply a device) is in electrical communication with a patient's heart 612 by way of three leads, 620, 624 and 630, suitable for delivering multi-chamber stimulation. While not necessary to perform embodiments of the present technology, the exemplary IMD 610 can also be capable of delivering shock therapy.

To sense atrial cardiac signals and to provide right atrial chamber stimulation therapy, the IMD 610 is coupled to an implantable right atrial lead 620 having at least an atrial tip electrode 622, which typically is implanted in the patient's right atrial appendage. To sense left atrial and ventricular cardiac signals and to provide left-chamber pacing therapy, the IMD 610 is coupled to a "coronary sinus" lead 624 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 624 is designed to receive left atrial and ventricular cardiac signals and to deliver left atrial and ventricular pacing therapy using at least a left ventricular tip electrode 626, left atrial pacing therapy using at least a left atrial ring electrode 627, and shocking therapy using at least a left atrial coil electrode 628. The present technology may of course be practiced with a coronary sinus lead that does not include left atrial sensing, pacing or shocking electrodes.

The IMD 610 is also shown in electrical communication with the patient's heart 612 by way of an implantable right ventricular lead 630 having, in this embodiment, a right ventricular tip electrode 632, a right ventricular ring electrode 634, a right ventricular (RV) coil electrode 636, and an SVC coil electrode 638. Typically, the right ventricular lead 630 is transvenously inserted into the heart 612 so as to place the right ventricular tip electrode 632 in the right ventricular apex so that the RV coil electrode 636 will be positioned in the right ventricle and the SVC coil electrode 638 will be positioned in the superior vena cava. Accordingly, the right ventricular lead 630 is capable of receiving cardiac signals and delivering stimulation in the form of pacing and shock therapy to the right ventricle. It will be understood by those skilled in the art that other lead and electrode configurations such as epicardial leads and electrodes may be used in practicing the technology. For example, only a single lead, or only two leads, may be connected to the IMD. It should also be understood that the IMD can alternatively be a leadless device, such as an implantable monitor and/or a leadless pacer. The various electrodes shown in and described with reference to FIG. 6 can be specific implementations of the electrodes 304 discussed above with reference to FIG. 3.

Figure 7:
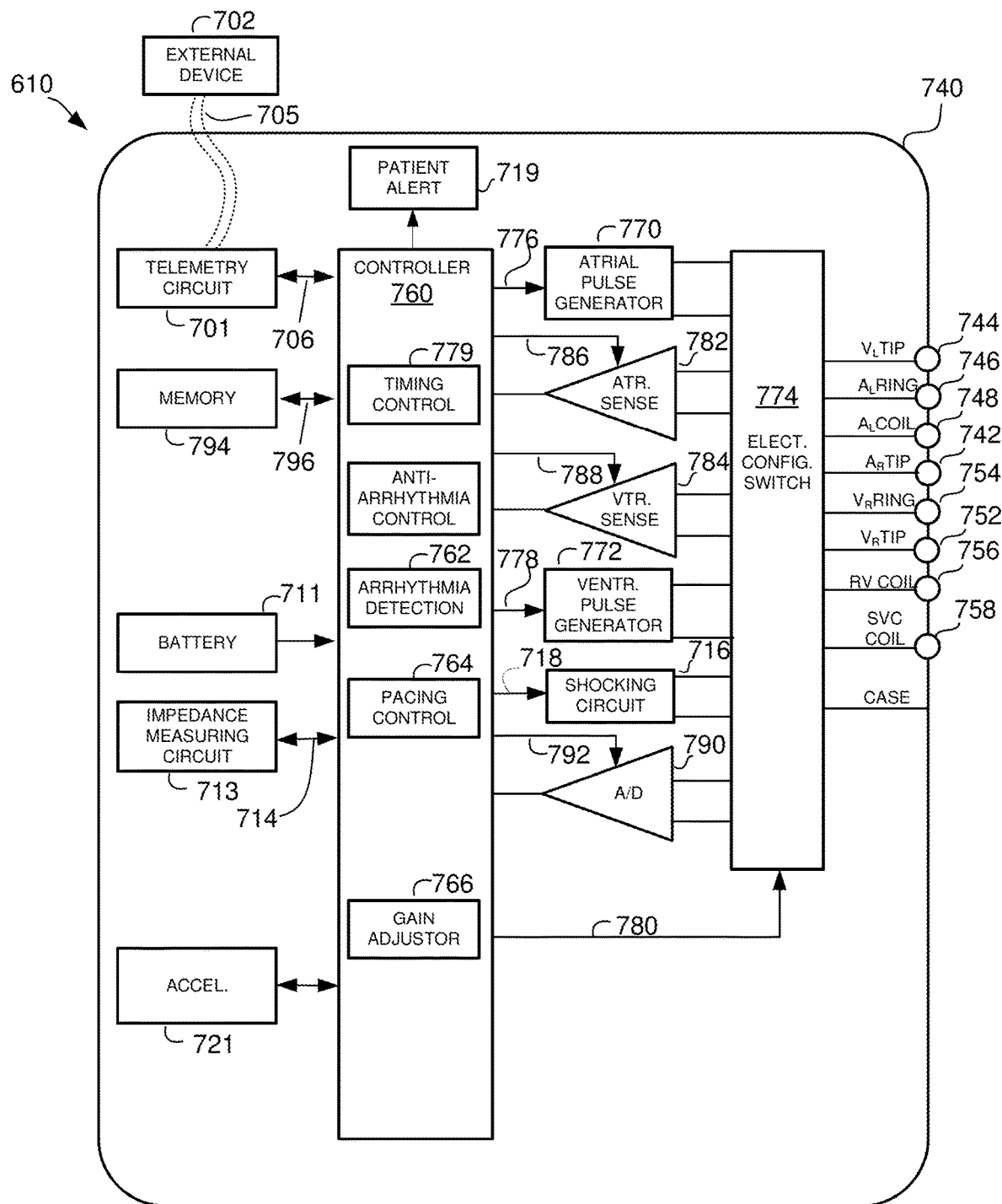
FIG. 7 is a simplified block diagram that is used to describe additional details of the IMD introduced in FIG. 7.

As illustrated in FIG. 7, a simplified block diagram is shown of the multi-chamber implantable device 610, which is capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation.

The housing 740 for the IMD 610, shown schematically in FIG. 7, is often referred to as the "can", "case" or "case electrode" and may be programable to electrically act as the return electrode for all "unipolar" modes. The housing 740 may further be used as a return electrode alone or in combination with one or more of the coil electrodes, 628, 636 and 638, for shocking purposes. The housing 740 further includes a connector (not shown) having a plurality of terminals, 742, 744, 746, 748, 752, 754, 756, and 758 (shown schematically and, for convenience, the names of the electrodes to which they are connected are shown next to the terminals). As such, to achieve right atrial sensing and pacing, the connector includes at least a right atrial tip terminal (AR TIP) 742 adapted for connection to the atrial tip electrode 622.

To achieve left atrial and ventricular sensing, pacing and shocking, the connector includes at least a left ventricular tip terminal (VL TIP) 744, a left atrial ring terminal (AL RING) 746, and a left atrial shocking terminal (AL COIL) 648, which are adapted for connection to the left ventricular ring electrode 626, the left atrial tip electrode 627, and the left atrial coil electrode 628, respectively.

To support right ventricle sensing, pacing and shocking, the connector further includes a right ventricular tip terminal (VR TIP) 752, a right ventricular ring terminal (VR RING) 754, a right ventricular shocking terminal (RV COIL) 756, and an SVC shocking terminal (SVC COIL) 758, which are adapted for connection to the right ventricular tip electrode 632, right ventricular ring electrode 634, the RV coil electrode 636, and the SVC coil electrode 638, respectively.

At the core of the IMD 610 is a programmable microcontroller 760 which controls the various types and modes of stimulation therapy. As is well known in the art, the microcontroller 760 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 760 includes the ability to process or monitor input signals (data) as controlled by a program code stored in a designated block of memory. The details of the design of the microcontroller 760 are not critical to the present technology. Rather, any suitable microcontroller 760 can be used to carry out the functions described herein. The use of microprocessor-based control circuits for performing timing and data analysis functions are well known in the art. In specific embodiments of the present technology, the microcontroller 760 performs some or all of the steps associated with arrhythmia detection. The microcontroller 760 can be used to implement that controller 334 discussed above with reference to FIG. 3.

Representative types of control circuitry that may be used with the technology include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the pacing device and their inter-relationship, see U.S. Pat. No. 4,788,980 (Mann et. al.). The '052, '555, '298 and '980 patents are incorporated herein by reference.

An atrial pulse generator 770 and a ventricular pulse generator 772 generate pacing stimulation pulses for delivery by the right atrial lead 620, the right ventricular lead 630, and/or the coronary sinus lead 624 via an electrode configuration switch 774. It is understood that in order to provide stimulation therapy in each of the four chambers of the heart, the atrial and ventricular pulse generators, 770 and 772, may include dedicated, independent pulse generators, multiplexed pulse generators, or shared pulse generators. The pulse generators, 770 and 772, are controlled by the microcontroller 760 via appropriate control signals, 776 and 778, respectively, to trigger or inhibit the stimulation pulses.

The microcontroller 760 further includes timing control circuitry 779 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 774 includes a plurality of switches for connecting the desired electrodes to the appropriate I/O circuits, thereby providing complete electrode programmability. Accordingly, the switch 774, in response to a control signal 780 from the microcontroller 760, determines the polarity of the stimulation pulses (e.g., unipolar, bipolar, etc.) by selectively closing the appropriate combination of switches (not shown) as is known in the art.

Atrial sensing circuits 782 and ventricular sensing circuits 784 may also be selectively coupled to the right atrial lead 620, coronary sinus lead 624, and the right ventricular lead 630, through the switch 774 for detecting the presence of cardiac activity in each of the four chambers of the heart. Accordingly, the atrial (ATR. SENSE) and ventricular (VTR. SENSE) sensing circuits, 782 and 784, may include dedicated sense amplifiers, multiplexed amplifiers, or shared amplifiers. The switch 774 determines the "sensing polarity" of the cardiac signal by selectively closing the appropriate switches, as is also known in the art. In this way, the clinician may program the sensing polarity independent of the stimulation polarity.

Each sensing circuit, 782 and 784, preferably employs one or more low power, precision amplifiers with programmable gain and/or automatic gain control, bandpass filtering, and a threshold detection circuit, as known in the art, to selectively sense the cardiac signal of interest. The automatic gain control enables the IMD 610 to deal effectively with the difficult problem of sensing the low amplitude signal characteristics of atrial or ventricular fibrillation. Such sensing circuits, 782 and 784, can be used to determine cardiac performance values used in the present technology. Alternatively, an automatic sensitivity control circuit may be used to effectively deal with signals of varying amplitude.

The outputs of the atrial and ventricular sensing circuits, 782 and 784, are connected to the microcontroller 760 which, in turn, are able to trigger or inhibit the atrial and ventricular pulse generators, 770 and 772, respectively, in a demand fashion in response to the absence or presence of cardiac activity, in the appropriate chambers of the heart. The sensing circuits, 782 and 784, in turn, receive control signals over signal lines, 786 and 788, from the microcontroller 760 for purposes of measuring cardiac performance at appropriate times, and for controlling the gain, threshold, polarization charge removal circuitry (not shown), and timing of any blocking circuitry (not shown) coupled to the inputs of the sensing circuits, 782 and 786. The sensing circuits can be used, for example, to acquire IEGM signals.

For arrhythmia detection, the IMD 610 includes an arrhythmia detector 762 that utilizes the atrial and ventricular sensing circuits, 782 and 784, to sense cardiac signals to determine whether a rhythm is physiologic or pathologic. The timing intervals between sensed events (e.g., P-waves, R-waves, and depolarization signals associated with fibrillation) are then classified by the microcontroller 760 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy"). The arrhythmia detector 762 can be implemented within the microcontroller 760, as shown in FIG. 7. Thus, this detector 762 can be implemented by software, firmware, or combinations thereof. It is also possible that all, or portions, of the arrhythmia detector 762 can be implemented using hardware. Further, it is also possible that all, or portions, of the arrhythmia detector 762 can be implemented separate from the microcontroller 760.

The stimulation device 610 is also shown as including a pacing controller 764, which can adjust a pacing rate and/or pacing intervals. The pacing controller 764 can be implemented within the microcontroller 760, as shown in FIG. 7. Thus, the pacing controller 764 can be implemented by software, firmware, or combinations thereof. It is also possible that all, or portions, of the pacing controller 764 can be implemented using hardware.

The accelerometer 721 of the IMD 610 can be or include, e.g., a MEMS (micro-electromechanical system) multi-axis accelerometer of the type exploiting capacitive or optical cantilever beam techniques, or a piezoelectric accelerometer that employs the piezoelectric effect of certain materials to measure dynamic changes in mechanical variables (e.g., acceleration, and/or vibration), but is not limited thereto. Depending upon implementation, the accelerometer 721 can be used to detect posture and/or motion of a patient in which an IMD 610 including the accelerometer 721 is implanted.

Additionally, the IMD 110 is shown as including a gain adjustor 766. In accordance with certain embodiments of the present technology, the gain adjustor 766 can be used adjust a gain applied an ECG/IEGM signal sensed using a pair of electrodes to thereby selectively adjust a sensitivity associated detecting R-waves by detecting crossings of fixed detection threshold. Additional details of the operation of the gain adjustor 766, according to various embodiments of the present technology, can be appreciated from the above discussion of FIGS. 3-5. The gain adjustor 766 can be implemented within the microcontroller 760, as shown in FIG. 7. Thus, the gain adjustor 766 can be implemented by software, firmware, hardware, or combinations thereof. It is also possible that all, or portions, of the gain adjustor 766 can be implemented using dedicated hardware, such as using an application specific integrated circuit (ASIC). More generally, the gain adjustor 766 can be implemented by a controller, wherein the controller may be a microcontroller (e.g., 760), or an ASIC, but is not limited thereto.

Still referring to FIG. 7, cardiac signals and/or other signals can be applied to the inputs of an analog-to-digital (A/D) data acquisition system 790. The data acquisition system 790 is configured to acquire intracardiac electrogram signals, convert the raw analog data into a digital signal, and store the digital signals for later processing and/or telemetric transmission to an external device 702. The data acquisition system 790 is coupled to the right atrial lead 620, the coronary sinus lead 624, and the right ventricular lead 630 through the switch 774 to sample cardiac signals across any pair of desired electrodes.

The data acquisition system 790 can be coupled to the microcontroller 760, or other detection circuitry, for detecting an evoked response from the heart 612 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 760 detects a depolarization signal during a window following a stimulation pulse, the presence of which indicates that capture has occurred. The microcontroller 760 enables capture detection by triggering the ventricular pulse generator 772 to generate a stimulation pulse, starting a capture detection window using the timing control circuitry 779 within the microcontroller 760, and enabling the data acquisition system 790 via control signal 792 to sample the cardiac signal that falls in the capture detection window and, based on the amplitude, determines if capture has occurred. The data acquisition system 790 may also be used to acquire signals produced by the sensors 719 and/or 721, and may convert analog signals produced by such sensor to digital signals. It is also possible that the sensors 719 and/or 721 output digital signals. The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present technology.

The converter and adjustable gain circuitry 324, described above with reference to FIG. 3, can be used to implement the data acquisition system 790 in FIG. 7, or vice versa. It would also be possible for the sense amplifier 308 in FIG. 3 to be used to implement the sensing circuit 782 and/or 784 in FIG. 7, or vice versa. Further, the electrode switch configuration bank 306 in FIG. 3 can be used to implement the electrode configuration switch 774 in FIG. 7, or vice versa. Similarly, the various electrodes shown in FIG. 6 and discussed with reference to FIGS. 6 and 7 can be the electrodes 304_1 ... 304_n in FIG. 3, or vice versa. Further, the controller 334 in FIG. 3 can be used to implement the microcontroller 760 in FIG. 7, or vice versa.

The microcontroller 760 is further coupled to the memory 794 by a suitable data/address bus 796, wherein the programmable operating parameters used by the microcontroller 760 are stored and modified, as required, in order to customize the operation of the IMD 610 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 612 within each respective tier of therapy. The memory 794 can also be used to store data relating to one or more magnetic field thresholds, and other information that can be utilized in embodiments of the present technology described herein.

The operating parameters of the IMD 610 may be non-invasively programmed into the memory 794 through a telemetry circuit 701 in telemetric communication with an external device 702, such as a programmer, transtelephonic transceiver, or a diagnostic system analyzer. The telemetry circuit 701 can be activated by the microcontroller 760 by a control signal 706. The telemetry circuit 701 advantageously allows intracardiac electrograms and status information relating to the operation of the device 610 (as contained in the microcontroller 760 or memory 794) to be sent to the external device 702 through an established communication link 704. The telemetry circuit 701 can also be used to trigger alarms or alerts of the external device 702, or to instruct the external device 702 to notify a caregiver regarding detection of various episodes, occurrences and changes in conditions that are detected using embodiments of the present technology.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The IMD 610 additionally includes a battery 711 which provides operating power to all of the circuits shown in FIG. 7. If the implantable device 610 also employs shocking therapy, the battery 711 should be capable of operating at low current drains for long periods of time, and then be capable of providing high-current pulses (for capacitor charging) when the patient requires a shock pulse. The battery 711 should also have a predictable discharge characteristic so that elective replacement time can be detected.

As further shown in FIG. 7, the IMD 610 is also shown as having an impedance measuring circuit 713 which is enabled by the microcontroller 760 via a control signal 714. The known uses for an impedance measuring circuit 713 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds and heart failure condition; detecting when the device has been implanted; measuring stroke volume; and detecting the opening of heart valves, etc. The impedance measuring circuit 713 is advantageously coupled to the switch 774 so that any desired electrode may be used. The impedance measuring circuit 713 is not critical to the present technology and is shown only for completeness.

In the case where the IMD 610 is also intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 760 further controls a shocking circuit 716 by way of a control signal 718. The shocking circuit 716 generates shocking pulses of low (up to 0.5 Joules), moderate (0.5-10 Joules), or high energy (11 to 40 Joules), as controlled by the microcontroller 760. Such shocking pulses are applied to the patient's heart 612 through at least two shocking electrodes, and as shown in this embodiment, selected from the left atrial coil electrode 728, the RV coil electrode 736, and/or the SVC coil electrode 738. As noted above, the housing 740 may act as an active electrode in combination with the RV electrode 736, or as part of a split electrical vector using the SVC coil electrode 738 or the left atrial coil electrode 728 (i.e., using the RV electrode as a common electrode).

The above described IMD 610 was described as an exemplary pacing device. One or ordinary skill in the art would understand that embodiments of the present technology can be used with alternative types of implantable devices. Accordingly, embodiments of the present technology should not be limited to use only with the above described device.

As noted above, embodiments of the present technology may also be used with a leadless pacemaker, or with an implantable cardiac monitor that does not provide any therapy. Exemplary leadless pacemakers are described in U.S. Pat. No. 8,996,109 (Karst et al.) and U.S. Pat. No. 9,533,163 (Klimovitch et al.), which are incorporated herein by reference. An implantable cardiac monitor that does not provide any therapy can, for example, store information indicative of R-waves, HR, HRV, as well as ECG/IEGM segments, and such stored information can be uploaded to an external device for analysis and or display.

Embodiments of the present technology describe above generally pertain to IMDs, and methods for use therewith. Such embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed technology. For example, it would be possible to combine or separate some of the steps shown in FIG. 5. For another example, it is possible to change the boundaries of some of the blocks shown in FIGS. 3 and 7.

It is noted that the term "base on", as used herein, should be interpreted as meaning based at least in part on, unless stated otherwise. In other words, where a decision is based on something, that decision can also be based on additional things. By contrast, where a decision is based solely on something, that decision is not also based on additional things.

The previous description of the preferred embodiments is provided to enable any person skilled in the art to make or use the embodiments of the present technology. While the technology has been particularly shown and described with reference to preferred embodiments thereof, it will be understood by those skilled in the art that various changes in form and details may be made therein without departing from the spirit and scope of the technology.

What is claimed is:

1. A method for dynamically controlling sensitivity associated with detecting R-waves, the method comprising:
   sensing an analog signal indicative of cardiac electrical activity;
   converting the analog signal indicative of cardiac electrical activity to a digital signal indicative of cardiac electrical activity;
   detecting R-waves in a digital domain by comparing the digital signal indicative of cardiac electrical activity to a fixed detection threshold to thereby detect threshold crossings in the digital domain that corresponds to R-waves; and
   selectively adjusting a gain applied to the digital signal indicative of cardiac electrical activity to thereby selectively adjust a sensitivity associated with the detecting R-waves in the digital domain, while maintaining the fixed detection threshold;
   wherein the selectively adjusting the gain occurs in the digital domain within a feedforward signal path, in-between where the converting and the detecting occur, downstream of the converting and upstream of the comparing.

2. The method of claim 1, wherein:
   the converting the analog signal indicative of cardiac electrical activity to the digital signal indicative of cardiac electrical activity is performed, at least in part, using an N-bit analog-to-digital converter (ADC) that accepts the analog signal indicative of cardiac electrical activity and outputs an N-bit digital signal;
   a course gain factor specifies which M-bits, of the N-bit digital signal output by the N-bit ADC, are used when comparing the digital signal indicative of cardiac electrical activity to the fixed detection threshold to thereby detect threshold crossings that corresponds to R-waves, where M<N; and
   the selectively adjusting the gain applied to the digital signal indicative of cardiac electrical activity is performed, at least in part, by selectively adjusting the course gain factor.

3. The method of claim 1, wherein:
   the converting the analog signal indicative of cardiac electrical activity to the digital signal indicative of cardiac electrical activity is performed using an N-bit analog-to-digital converter (ADC) and a multiplier downstream of the N-bit ADC;
   the N-bit ADC accepts the analog signal indicative of cardiac electrical activity and outputs an N-bit digital signal;
   a course gain factor specifies which M-bits, of the N-bit digital signal output by the N-bit ADC, is provided to the multiplier, where M<N;
   a fine gain factor specifies a value that the M-bits, provided to the multiplier, are multiplied by to produce the digital signal indicative of cardiac electrical activity that is compared to the fixed detection threshold to detect R-waves; and
   the selectively adjusting the gain applied to the digital signal is performed, at least in part, by selectively adjusting the fine gain factor.

4. The method of claim 3, wherein:
   the selectively adjusting the gain applied to the digital signal is also performed, at least in part, by selectively adjusting the course gain factor.

5. The method of claim 3, further comprising:
   detecting peak amplitudes of the digital signal indicative of cardiac electrical activity, by detecting a peak amplitude of the digital signal indicative of cardiac electrical activity within a window following a said threshold crossing, each time the comparing results in a said threshold crossing that corresponds to an R-wave;
   wherein the selectively adjusting the fine gain factor is based on the peak amplitudes of the digital signal indicative of cardiac electrical activity.

6. The method of claim 5, wherein the selectively adjusting the fine gain factor comprises:
   adjusting the fine gain factor in response to a said peak amplitude, of the digital signal indicative of cardiac electrical activity, being outside a specified range; and
   not adjusting the fine gain factor in response to a said peak amplitude, of the digital signal indicative of cardiac electrical activity, being within the specified range.

7. The method of claim 6, wherein the adjusting the fine gain factor in response to a said peak amplitude, of the digital signal indicative of cardiac electrical activity, being outside the specified range, comprises:
   decreasing the fine gain factor in response to a said peak amplitude, of the digital signal indicative of cardiac electrical activity, being above the specified range; and
   increasing the fine gain factor in response to a said peak amplitude, of the digital signal indicative of cardiac electrical activity, being below the specified range.

8. The method of claim 1, wherein:
   the converting the analog signal indicative of cardiac electrical activity to the digital signal indicative of cardiac electrical activity, which is compared to the fixed detection threshold to detect R-waves, is performed using an analog-to-digital converter (ADC) and a multiplier downstream of the ADC;

the ADC accepts the analog signal indicative of cardiac electrical activity and outputs a digital signal;
the digital signal that is output by the ADC is multiplied by a value to produce the digital signal indicative of cardiac electrical activity that is compared to the fixed detection threshold to detect R-waves; and
the selectively adjusting the gain is performed, at least in part, by selectively adjusting the value that is multiplied by the digital signal output by the ADC.

9. The method of claim 1, further comprising specifying the fixed detection threshold during manufacture of a device that implements the method, during calibration of a device that implements the method, prior to implantation of a device that implements the method, or after implantation of a device that implements the method.

10. The method of claim 1, further comprising:
measuring RR intervals based on detected R-waves;
monitoring for one or more types of arrhythmias based on the RR intervals; and
triggering an action in response to a said arrhythmia being detected.

11. A device capable of dynamically controlling sensitivity associated with detecting R-waves, the device comprising:
a plurality of electrodes;
a sense amplifier configured to be coupled to a pair of the electrodes and configured to output an analog signal indicative of cardiac electrical activity;
an analog-to-digital converter (ADC) configured to convert the analog signal indicative of cardiac electrical activity to a digital signal indicative of cardiac electrical activity;
adjustable gain circuitry downstream of the ADC and configured to adjust a gain applied to the digital signal indicative of cardiac electrical activity;
a digital comparator downstream of the adjustable gain circuitry and configured to detect R-waves by comparing the digital signal indicative of cardiac electrical activity to a fixed detection threshold to thereby detect threshold crossings that corresponds to R-waves; and
a controller configured to selectively adjust the gain applied by the adjustable gain circuitry to thereby selectively adjust a sensitivity associated with the comparator detecting R-waves by detecting threshold crossings that corresponds to R-waves;
wherein the ADC, the adjustable gain circuitry downstream of the ADC, and the digital comparator downstream of the adjustable gain circuitry, are all included in a feedforward signal path; and
wherein the adjustable gain circuitry, for which gain is selectively adjusted by the controller, is between the ADC and the digital comparator within the feedforward signal path, downstream of the ADC and upstream of the digital comparator.

12. The device of claim 11, wherein:
the ADC comprise an N-bit ADC; and
the adjustable gain circuitry comprises both an M-bit selector and a multiplier downstream of the N-bit ADC.

13. The device of claim 12, wherein:
the M-bit selector is configured to select which M-bits of an N-bit digital signal output by the N-bit ADC is provided to the multiplier, where M<N; and
the multiplier is configured to multiplying the M-bits, selected by the M-bit selector, by a value provided to the multiplier by the controller; and the controller is configured to perform one or more course gain adjustments by changing which M-bits of the N-bit digital signal output by the N-bit ADC is provided to the multiplier.

14. The device of claim 12, wherein:
the controller is configured to perform one or more fine gain adjustments by selectively changing the value, provided to the multiplier, that is multiplied by the M-bits selected by the M-bit selector.

15. The device of claim 11, wherein:
the adjustable gain circuitry comprises a multiplier downstream of the ADC; and
the controller is configured to adjust the gain applied by the adjustable gain circuitry by changing a value that is provided to the multiplier to multiply by a digital signal output by the ADC or by a digital signal output by an M-bit selector between the ADC and the multiplier.

16. The device of claim 11, wherein the controller is further configured to:
measure RR intervals based on detected R-waves;
monitor for one or more types of arrhythmias based on the RR intervals; and
trigger an action in response to a said arrhythmia being detected.

17. A device capable of detecting R-waves, the device comprising:
a plurality of electrodes;
a sense amplifier configured to be coupled to a pair of the electrodes and configured to output an analog signal indicative of cardiac electrical activity;
converter and adjustable gain circuitry configured to convert the analog signal indicative of cardiac electrical activity to a digital signal indicative of cardiac electrical activity and to selectively adjust at least one adjustable gain factor in the digital domain;
digital comparator circuitry configured to detect R-waves by comparing the digital signal indicative of cardiac electrical activity to a fixed detection threshold to thereby detect threshold crossings that corresponds to R-waves; and
a controller configured to selectively adjust the at least one adjustable gain factor of the converter and adjustable gain circuitry to thereby selectively adjust a sensitivity associated with detecting R-waves;
wherein the converter and adjustable gain circuitry, for which the at least one adjustable gain factor is adjusted in the digital domain by the controller, is within a feedforward path between the sense amplifier and the digital comparator circuitry, downstream of the sense amplifier and upstream of the digital comparator.

18. The device of claim 17, wherein:
the at least one gain factor that is adjusted, to selectively adjust the sensitivity associated with detecting R-waves, comprises at least one of a fine gain factor or a course gain factor.

19. The device of claim 18, wherein the converter and adjustable gain circuitry comprises:
an N-bit analog-to-digital converter (ADC) configured to accept the analog signal indicative of cardiac electrical activity and output an N-bit digital signal; and
a multiplier downstream of the N-bit ADC;
wherein the course gain factor specifies which M-bits of, the N-bit digital signal output by the N-bit ADC, is provided to the multiplier, where M<N; and
wherein the fine gain factor specifies a digital value that the M-bits, provided to the multiplier, are multiplied by to produce the digital signal indicative of cardiac electrical activity that the comparator circuitry compares to the fixed detection threshold to detect R-waves.

20. The device of claim 19, wherein:

the converter and adjustable gain circuitry further comprise an M-bit selector between the N-bit ADC and the multiplier; and the controller provides the course gain factor to the M-bit selector to control which M-bits, of the N-bit digital signal output by the N-bit ADC, is provided to the multiplier.

21. The device of claim 19, wherein:

the controller is configured to selectively adjust the fine gain factor based on peak amplitudes of the digital signal indicative of cardiac electrical activity to thereby selectively adjust the sensitivity associated with detecting R-waves.

22. The device of claim 18, wherein the converter and adjustable gain circuitry comprises:

an analog-to-digital converter (ADC) configured to accept the analog signal indicative of cardiac electrical activity and output a digital signal; and a multiplier downstream of the ADC;

wherein the controller is configured to selectively adjust at least one gain factor of the converter and adjustable gain circuitry by selectively adjust a digital value that the controller provides to the multiplier, to multiply by the digital signal output by the ADC, to produce the digital signal indicative of cardiac electrical activity that the comparator circuitry compares to the fixed detection threshold to detect R-waves.

23. The device of claim 18, wherein the converter and adjustable gain circuitry comprises:

an analog-to-digital converter (ADC) configured to accept the analog signal indicative of cardiac electrical activity and output a digital signal;

a multiplier downstream of the ADC; and an M-bit selector downstream of the multiplier;

wherein the controller is configured to selectively adjust at least one gain factor of the converter and adjustable gain circuitry by selectively adjusting a digital value that the controller provides to the multiplier, to multiply by the digital signal output by the ADC.

24. The device of claim 23, wherein the controller is also configured to selectively adjust at least one further gain factor of the converter and adjustable gain circuitry by selectively adjusting which M-bits of N-bits output by the multiplier are provided to the comparator as the digital signal indicative of cardiac electrical activity.

\* \* \* \* \*